United States Patent

Ralph

Patent Number: 5,931,841
Date of Patent: Aug. 3, 1999

[54] COMBINATION BROACHER-REAMER FOR USE IN ORTHOPAEDIC SURGERY

[75] Inventor: Christopher R. Ralph, West Milford, N.J.

[73] Assignee: Stryker Technologies Corporation, Kalamazoo, Mich.

[21] Appl. No.: 09/066,243

[22] Filed: Apr. 24, 1998

[51] Int. Cl.$^6$ .................................................. A61B 17/16
[52] U.S. Cl. .............................. 606/85; 606/80; 408/225; 407/18
[58] Field of Search .................................. 606/79, 80, 84, 606/85; 407/12, 18, 19; 408/223, 224, 225; 433/102

[56] References Cited

U.S. PATENT DOCUMENTS

| | | |
|---|---|---|
| 2,643,443 | 6/1953 | LaPointe et al. . |
| 4,124,026 | 11/1978 | Berner et al. . |
| 4,552,136 | 11/1985 | Kenna . |
| 5,041,118 | 8/1991 | Wasilewski ............................ 606/85 |
| 5,503,506 | 4/1996 | Yuan . |

*Primary Examiner*—Michael Buiz
*Assistant Examiner*—David O. Reip
*Attorney, Agent, or Firm*—Lerner, David, Littenburg, Krumholz & Mentlik, LLP

[57] ABSTRACT

A combination broacher-reamer includes a generally longitudinally symmetrical cutting tool which is provided with a plurality of longitudinal broaching cutting teeth as well as a plurality of axial reaming cutting teeth. According to a presently preferred embodiment, the broacher-reamer is generally cylindrical with a smooth blunt distal tip and a tapered distal cutting portion. The proximal end of the tool is provided with a handle and one or more witness marks are provided on the shank of the tool. If the handle is removable the shank may be coupled to a motor or impacting tool. An exemplary broacher-reamer according to the invention is approximately 6.78 inches long with an overall maximum diameter of approximately 0.843 inches. The proximal end of the tool has a diametrical throughbore which is dimensioned to receive the handle which is approximately 3.94 inches long. The cutting portion of the tool begins approximately 3.0 inches distal of the proximal end and terminates approximately 1.25 inches short of the blunt smooth distal end of the tool. The reaming cutting teeth are arranged in a plurality of helical paths which transect the broaching teeth, each helical path being offset from an adjacent path by approximately 36 degrees and having a right hand helix angle of approximately 28 degrees. The flutes of the reaming teeth are the same depth as and are interrupted by the spaces (fillets) between the broaching teeth.

21 Claims, 5 Drawing Sheets

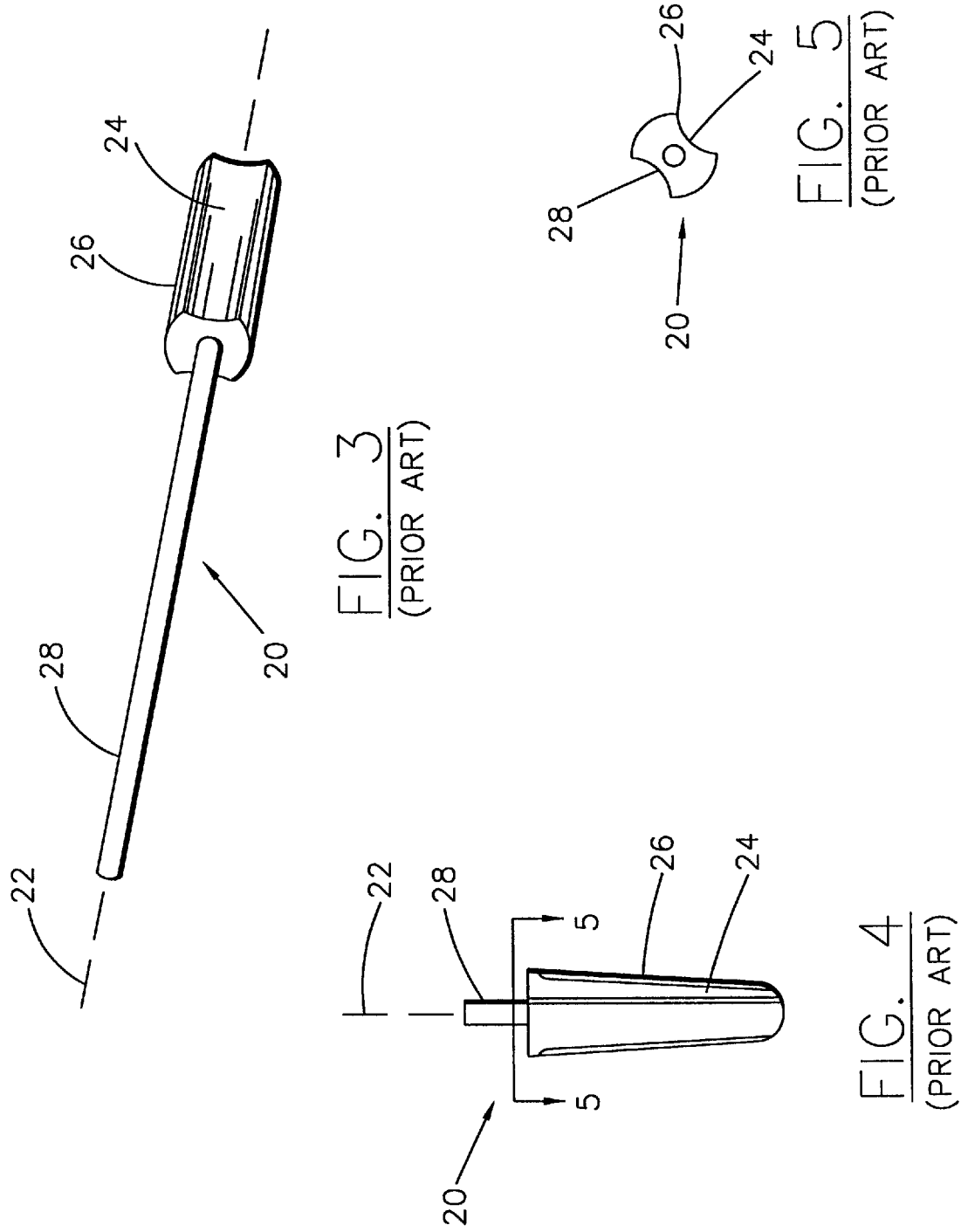

COMBINATION BROACHER-REAMER FOR USE IN ORTHOPAEDIC SURGERY

BACKGROUND OF THE INVENTION

1. Field of the Invention

The invention relates to orthopaedic surgery. More particularly, the invention relates to tools used to prepare bones for orthopaedic implants.

2. Brief Description Of The Prior Art

Orthopaedic implant surgery typically involves the preparation of one or more bones to receive an implant stem or rod. For example, the installation of prosthetic hips and knees requires that the intramedullary (IM) canal of the femur be hollowed in order to accept the stem of a prosthetic implant. In general, the preparation of the IM canal involves the displacement of cancellous bone in order to create a cavity which will receive the stem of the implant. These cavities are usually created by one of two methods: broaching or reaming.

Broaching and reaming are quite different procedures, each having its own advantages and disadvantages. Prior art FIGS. 1 and 2 show a typical broaching tool and prior art FIGS. 3–5 show a typical reaming tool.

The broacher 10 shown in FIGS. 1 and 2 generally includes a plurality of parallel teeth 12, each having a sharp distal cutting edge 14 which is formed by distal flaring. The teeth 12 are spaced along an axis 16 of the broacher and the broacher is typically asymmetrical about the axis 16 as shown by comparing FIGS. 1 and 2. As such, the broacher 12 is well suited for creating an asymmetrical canal.

The broacher 10 is generally introduced into a pre-drilled bone canal with the aid of an impactor tool such as a hammer (not shown). The sharp edges 14 of the teeth 12 engage cancellous bone axially and displace the soft bone material within the canal. The broaching procedure may displace cancellous bone material within the bone in order to create a cavity for receipt of the stem of an implant.

Those skilled in the art will appreciate that the asymmetrical geometry of the broacher 10 may be considered either an advantage or a disadvantage depending on the surgical situation. In addition, it will be understood that the displacement of cancellous bone without removing it may also be considered an advantage or a disadvantage depending on the particular surgical situation. If the bone is structurally weak, it may be desirable to avoid removing any of the cancellous bone material. If the bone is not weak and the cancellous bone material is diseased, it may be more desirable to remove the cancellous bone material.

The reamer 20 shown in FIGS. 3–5 is generally symmetrical about its longitudinal axis 22 and is provided with at least one substantially longitudinal flute 24 defining a sharp cutting edge 26 which extends generally longitudinally along substantially the entire cutting portion of the tool. The reamer 20 has a shaft 28 which allows it to be rotated about its longitudinal axis 22 with the aid of a handle or a motor (not shown).

Those skilled in the art will know that the reamer may be provided with plural flutes and the flutes may be helically arranged. Moreover, each flute may define either one or two cutting edges. If the flutes each define only one cutting edge, the reamer will cut bone only when rotated in one (clockwise or counter-clockwise) direction. If the flutes each define two cutting edges, the reamer will cut bone when rotated in either (clockwise or counter-clockwise) direction. The cutting edges in the reamer engage the cancellous bone radially and usually displace the cut bone axially to the proximal end of the tool such that the bone is removed from the reamed canal.

It will be appreciated that the symmetrical geometry of the reamer 20 may be considered either an advantage or a disadvantage depending on the surgical situation. In addition, it will be understood that the removal of cancellous when creating a cavity for the stem of an implant may also be considered an advantage or a disadvantage depending on the particular surgical situation.

From the foregoing, it will be understood that many of the features of broachers and reamers are mutually exclusive. For example, if it is desirable to create a symmetrical cavity without removing cancellous bone material, neither the broacher nor the reamer may accomplish that result. Moreover, if it is desirable to remove some, but not all, cancellous bone material, a surgeon may need to use both a broacher and a reamer in the same bone canal.

SUMMARY OF THE INVENTION

It is therefore an object of the invention to provide a surgical tool which combines features of a broacher and a reamer.

It is also an object of the invention to provide a combined broacher-reamer which allows the surgeon to remove some, but not all, of the cancellous bone when preparing a canal for receipt of the stem of an implant.

It is another object of the invention to provide a broaching tool which can be used to form a symmetrical cavity.

In accord with these objects which will be discussed in detail below, the combination broacher-reamer of the present invention includes a generally longitudinally symmetrical cutting tool which is provided with a plurality of longitudinal broaching cutting teeth as well as a plurality of axial reaming cutting teeth. According to a presently preferred embodiment, the broacher-reamer is generally cylindrical with a smooth blunt distal tip and a tapered distal cutting portion. A handle (fixed or removable) is provided below the proximal end of the tool and one or more witness marks are provided on the shaft of the tool between the handle and the cutting portion.

An exemplary broacher-reamer according to the invention is approximately 6.78 inches long with an overall maximum diameter of approximately 0.843 inches. The proximal end of the tool, prior to assembly, has a diametrical throughbore which is dimensioned to receive the handle which is approximately 3.94 inches long. The cutting portion of the tool begins approximately 3.0 inches distal of the proximal end and terminates approximately 1.25 inches short of the blunt smooth distal end of the tool.

The broaching cutting teeth are spaced approximately 0.090 inches apart (i.e., have a pitch of approximately 0.090), have a land width of approximately 0.010 inches, are flared at an angle of approximately 40 degrees, are approximately 0.060 inches deep, and have a tooth fillet radius of approximately 0.020 inches.

The reaming cutting teeth are arranged in a plurality of helical paths which transect the broaching teeth, each helical path being offset from an adjacent path by approximately 36 degrees and having a right hand helix angle of approximately 28 degrees. The flutes of the reaming teeth are the same depth as and interrupted by the spaces (fillets) between the broaching teeth.

Additional objects and advantages of the invention will become apparent to those skilled in the art upon reference to the detailed description taken in conjunction with the provided figures.

BRIEF DESCRIPTION OF THE DRAWINGS

FIG. 3 is a perspective view of a prior art reamer;

FIG. 4 is a broken side elevation view of the prior art reamer of FIG. 3;

FIG. 5 is a view taken along line 5—5 in FIG. 4;

DETAILED DESCRIPTION

Figure 6:
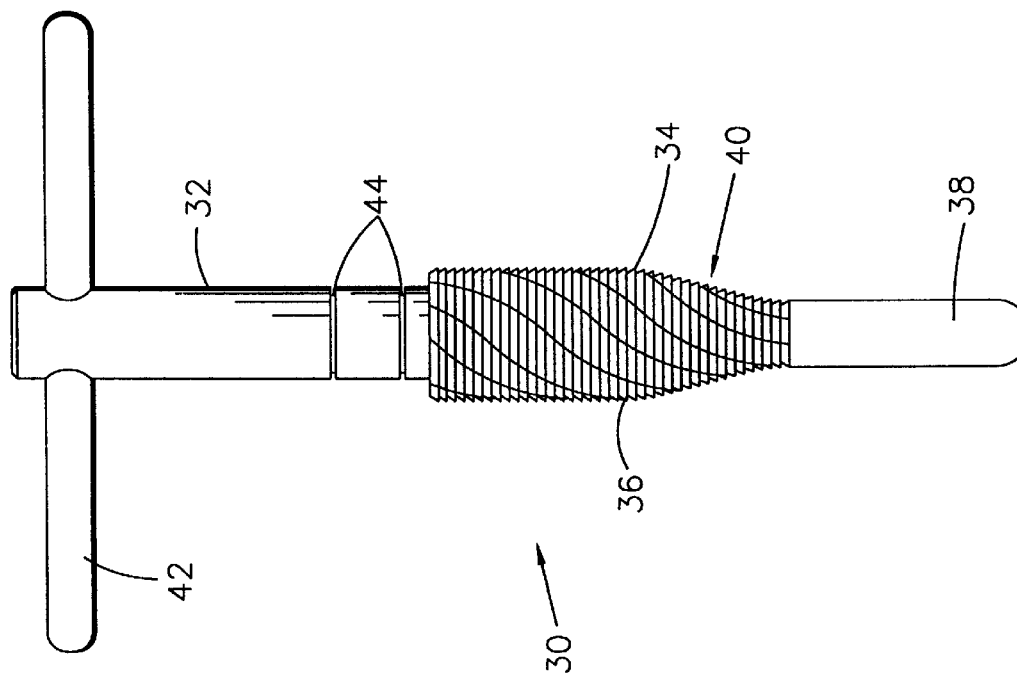
FIG. 6 is a side elevation view of a combination broacher-reamer according to the invention.
Figure 9:
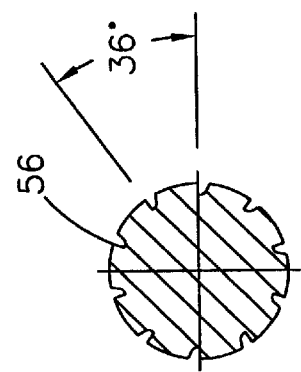
FIG. 9 is an enlarged section taken along the line 9—9 in FIG. 8.

Referring now to FIG. 6, a combination broacher-reamer 30 according the present invention includes a generally longitudinally symmetrical cutting tool having a shank 32, a plurality of longitudinal broaching cutting teeth 34 as well as a plurality of axial reaming cutting teeth 36.

According to a presently preferred embodiment, the broacher-reamer 30 is generally cylindrical with a smooth blunt distal tip 38 and a tapered distal cutting portion 40. The shank 32 of the tool is provided with a handle 42 and one or more witness marks 44 are provided on the shank of the tool. If the handle is removable shank 32 of the tool may be coupled to a motor or impacting tool. The witness marks are provided as an indication to the surgeon of the depth of the canal being reamed/broached.

FIGS. 7–13 illustrate a presently preferred embodiment 50 of a broacher-reamer according to the invention. As shown generally in FIG. 7, the broacher-reamer 50 includes a generally longitudinally symmetrical cutting tool having a shank 52, a plurality of longitudinal broaching cutting teeth 54 as well as a plurality of axial reaming cutting teeth 56.

According to a presently preferred embodiment, the broacher-reamer 50 is generally cylindrical with a smooth blunt distal tip 58 and a tapered distal cutting portion 60. The shank 52 of the tool is provided with a removable handle 62 and one or more witness marks 64 are provided on the shank 52 of the tool. It will be appreciated that the broacher-reamer 50 is similar to the broacher reamer 30 but with some apparent differences.

It will be observed that the dimensions and particular geometry of the cutting teeth as well as their locations relative to the tool and to each other are different from the dimensions, geometry, and locations of the teeth on the broacher-reamer 30. The broacher-reamer 50 is the presently preferred embodiment of the invention and the embodiment shown in FIG. 6 is a prototype of the concept of the invention.

Turning now to FIGS. 8–13, the presently preferred broacher-reamer 50 is approximately 6.78 inches long with an overall maximum diameter of approximately 0.843 inches and a minimum diameter of approximately 0.428 inches. The proximal end of the shank 52, prior to assembly, has a diametrical throughbore 66 which is dimensioned to receive the removable handle (62 in FIG. 7) which is approximately 3.94 inches long with a diameter of approximately 0.375 inches. The shank portion 52 of the tool 50 is approximately 3.0 inches long and the blunt smooth distal end of the tool is approximately 1.25 inches long.

The broaching cutting teeth 54 are spaced approximately 0.090 inches apart (i.e., have a pitch of approximately 0.090), have a land width of approximately 0.010 inches, are flared at an angle of approximately 40 degrees (with a clearance angle of approximately 0 degrees 37 minutes, are approximately 0.060 inches deep, and have a tooth fillet radius of approximately 0.020 inches.

The reaming cutting teeth 56 are arranged in a plurality of helical paths which transect the broaching teeth 54, each helical path being offset from an adjacent path by approximately 36 degrees and having a right hand helix angle of approximately 28 degrees. The flutes of the reaming teeth 56 are the same depth as and are interrupted by the spaces (fillets) between the broaching teeth 54.

Figure 2:
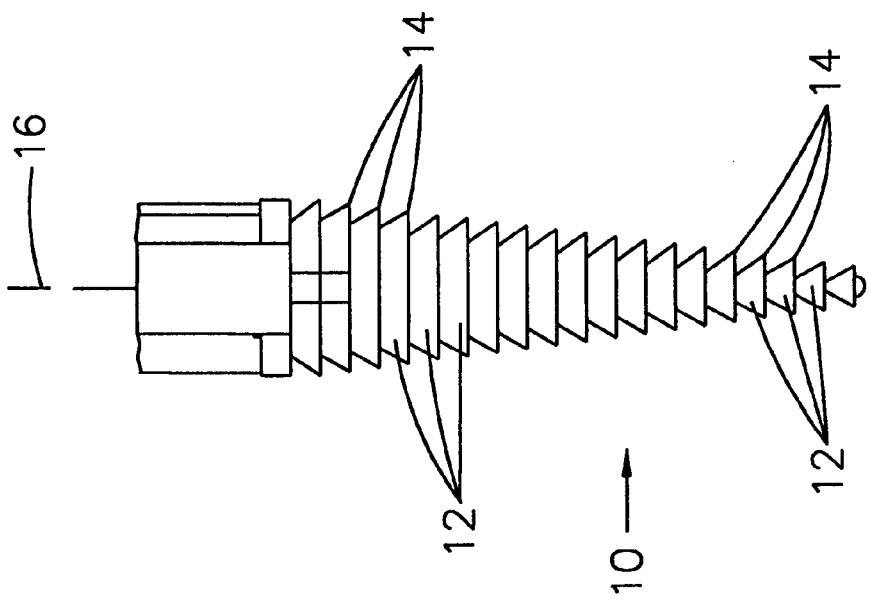
FIG. 2 is a view taken along line 2—2 of the broacher of FIG. 1.
Figure 1:
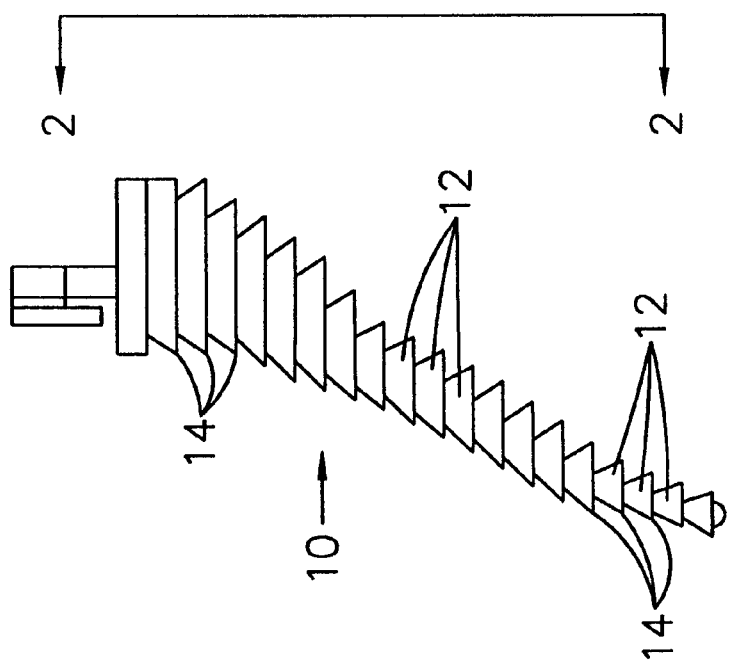
FIG. 1 is a broken side elevation view of a prior art broacher.
Figure 7:
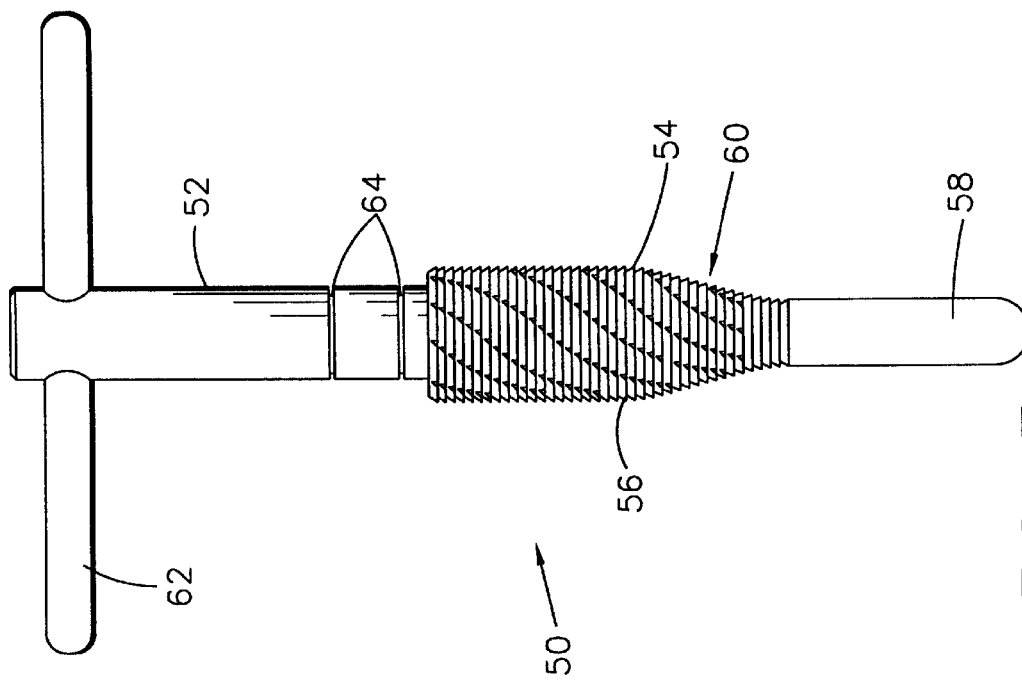
FIG. 7 is a view similar to FIG. 6 of a presently preferred embodiment of the invention.
Figure 8:
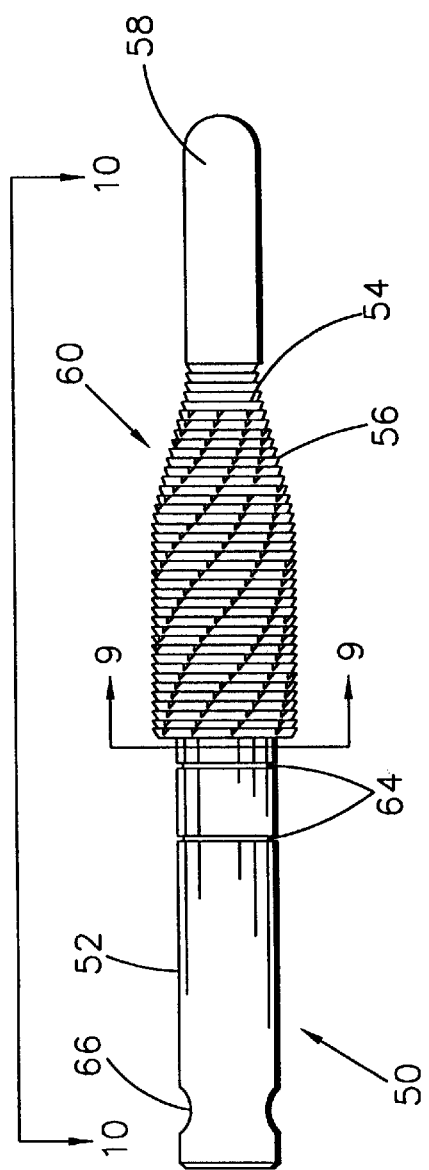
FIG. 8 is a side elevation view of the broacher-reamer of FIG. 7 with the handle removed.
Figure 10:
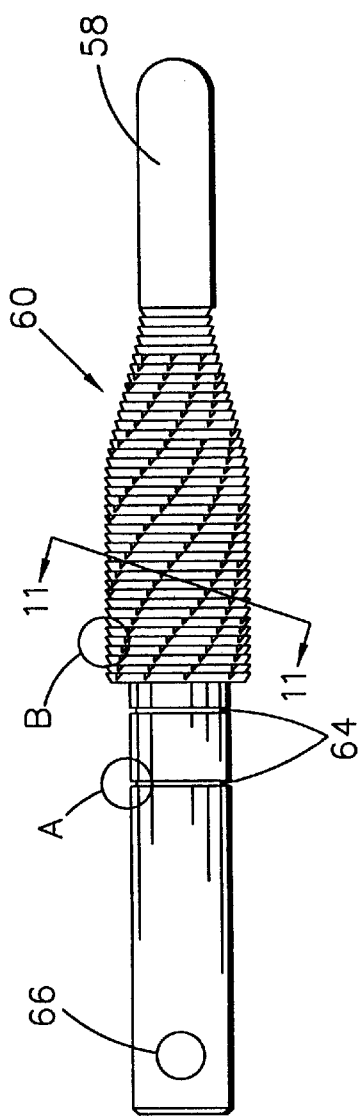
FIG. 10 is a view taken along the line 10—10 in FIG. 8.
Figure 13:
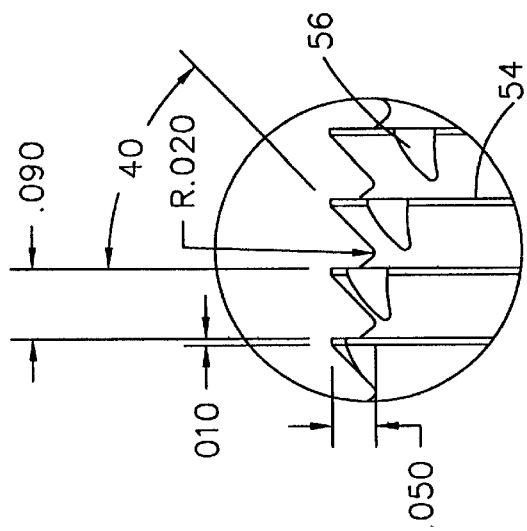
FIG. 13 is an enlarged view of the circled detail "B" in FIG. 10.
Figure 12:
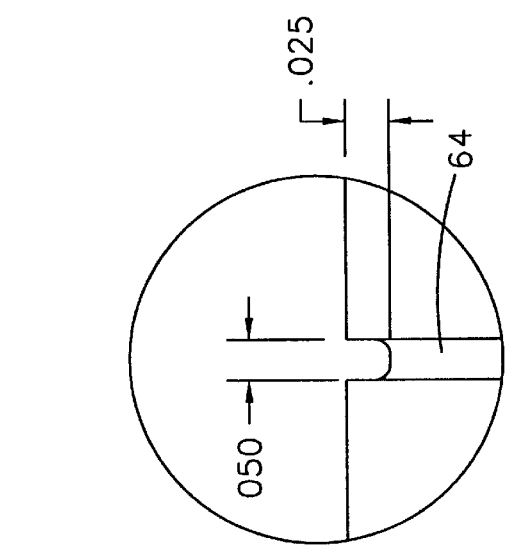
FIG. 12 is an enlarged view of the circled detail "A" in FIG. 10.
Figure 11:
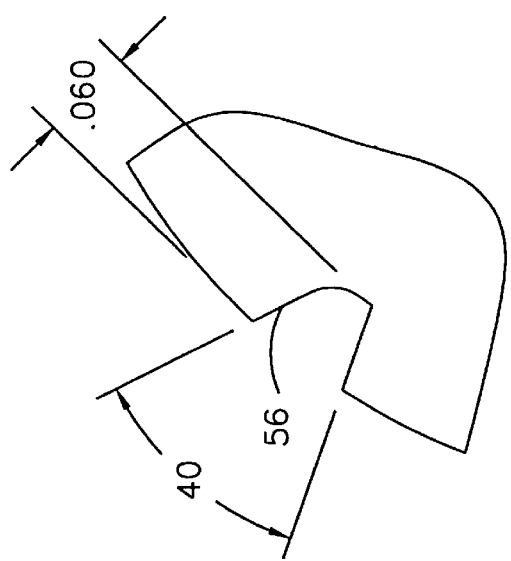
FIG. 11 is a broken enlarged section taken along the line 11—11 in FIG. 8.

According to the presently preferred embodiment, the cutting teeth 54 and 56 are diametrically tapered toward the smooth distal tip 58 of the tool 50. As shown in FIGS. 7, 8, and 10, the tapering is effected along a first convex radius of approximately 1.75 inches and a second concave radius of approximately 1.25 inches which reduces the diameter of the tool 50 from its maximum diameter of 0.843 inches to its minimum diameter of 0.428 inches.

As seen in the FIGS., the tapering results in the reaming teeth 56 being discontinued at a point spaced apart from the smooth blunt tip portion 58 and provides approximately four distal broaching teeth which are not transected by reaming teeth. It will be appreciated that the four distal broaching teeth have land diameters substantially equal to the minimum diameter (0.428) of the tool.

As mentioned above, it is preferred to provide at least one witness mark 64 on the shank portion 52 of the tool 50. The witness mark(s) is used to indicate to the practitioner the depth to which the tool 50 has been inserted into a bone canal. The marks shown in the FIGS. are engraved to a depth of approximately 0.025 inches and are located at 11 mm and 15 mm from the distal end of the shank 52.

Those skilled in the art will appreciate from the foregoing disclosure that the combination broacher-reamer of the invention allows the broaching of a symmetrical cavity and allow the surgeon to combine broaching and reaming in a single operation such that some, but not all of the cancellous bone may be removed from the canal.

There have been described and illustrated herein several embodiments of a combination broacher-reamer for use in orthopaedic surgery. While particular embodiments of the invention have been described, it is not intended that the invention be limited thereto, as it is intended that the invention be as broad in scope as the art will allow and that the specification be read likewise. It will therefore be appreciated by those skilled in the art that yet other modifications could be made to the provided invention without deviating from its spirit and scope as so claimed.

What is claimed is:

1. A combination orthopaedic surgical broaching and reaming tool comprising a substantially cylindrical tool having a proximal shank portion adapted to internally receive a handle, a plurality of axially spaced substantially parallel broaching teeth, and plurality of reaming teeth, said reaming teeth transecting at least some of said broaching teeth.

2. A tool according to claim 1 further comprising a substantially smooth and blunt distal tip serving as a guide for the tool.

3. A tool according to claim 2 wherein said shank portion has a first diameter and said distal tip has a second diameter smaller than said first diameter.

4. A tool according to claim 3 wherein at least some of said broaching teeth have a third diameter larger than said first diameter.

5. A tool according to claim 4 wherein at least some of said broaching teeth have a fourth diameter smaller than said first diameter and larger than said second diameter.

6. A tool according to claim 5 wherein at least some of said broaching teeth have a fifth diameter substantially equal to said second diameter.

7. A tool according to claim 1 wherein said plurality of reaming teeth are arranged along at least one helical path.

8. A tool according to claim 7 wherein said plurality of reaming teeth are arranged along ten angularly spaced apart helical paths.

9. A tool according to claim 7 wherein said at least one helical path has a helix angle of approximately 28 degrees.

10. A tool according to claim 1 further comprising a removable handle removably couplable to said shank portion.

11. A tool according to claim 1 further comprising a fixed handle affixed to said shank portion.

12. A tool according to claim 10 wherein said shank portion is provided with a diametrical throughbore and said removable handle is dimensioned to fit therethrough.

13. A tool according to claim 11 wherein said shank portion is provided with a diametrical throughbore and said fixed handle is dimensioned to fit therethrough.

14. A tool according to claim 1 further comprising at least one witness mark on said shank portion.

15. A combination orthopaedic surgical broaching and reaming tool comprising a generally cylindrical tool having a proximal shank portion, a plurality of axially spaced substantially parallel broaching teeth, a plurality of reaming teeth, said reaming teeth transecting at least some of said broaching teeth, and a substantially smooth and blunt distal tip; said shank portion having a first diameter and said distal tip having a second diameter smaller than said first diameter; at least some of said broaching teeth having a third diameter larger than said first diameter; at least some of said broaching teeth having a fourth diameter smaller than said first diameter and larger than said second diameter; and at least some of said broaching teeth having a fifth diameter substantially equal to said second diameter.

16. A tool according to claim 15 wherein said plurality of reaming teeth are arranged along ten angularly spaced apart helical paths, each having a helix angle of approximately 28 degrees.

17. A tool according to claim 15 further comprising a removable handle removably couplable to said shank portion.

18. A tool according to claim 15 further comprising a fixed handle affixed to said shank portion.

19. A tool according to claim 17 wherein said shank portion is provided with a diametrical throughbore and said removable handle is dimensioned to fit through said throughbore.

20. A tool according to claim 18 wherein said shank portion is provided with a diametrical throughbore and said fixed handle is dimensioned to fit through said throughbore.

21. A tool according to claim 15 further comprising at least one witness mark on said shank portion.

\* \* \* \* \*

UNITED STATES PATENT AND TRADEMARK OFFICE
CERTIFICATE OF CORRECTION

PATENT NO. : 5,931,841
DATED : August 3, 1999
INVENTOR(S) : Ralph

It is certified that error appears in the above-identified patent and that said Letters Patent is hereby corrected as shown below:

Column 2, line 7, after "cancellous", insert -- bone material --.
Column 3, line 30, after "according", insert -- to --.
Column 4, line 14, after "minutes", insert -- ) --.
Column 4, line 50, "allow" should read -- allows --.

Signed and Sealed this

Thirtieth Day of January, 2001

Q. TODD DICKINSON

Attest:

Attesting Officer

Director of Patents and Trademarks